United States Patent [19]

Rodriguez et al.

[11] 4,443,460  
[45] Apr. 17, 1984

[54] 2-[4-(DIPHENYLMETHYLENE)-1-PIPERIDINYL]-ACETIC ACIDS AND THEIR AMIDES

[75] Inventors: Ludovic Rodriguez, Brussels; Eugène Baltes, Rhode-St. Genese, both of Belgium

[73] Assignee: UCB, Societe Anonyme, Brussels, Belgium

[21] Appl. No.: 303,522

[22] Filed: Sep. 17, 1981

[30] Foreign Application Priority Data

Sep. 18, 1980 [GB] United Kingdom ............... 8030194

[51] Int. Cl.$^3$ ................. A61K 31/445; C07D 211/22
[52] U.S. Cl. .................................. 424/267; 546/239; 546/234
[58] Field of Search ................. 546/239, 234; 424/267

[56] References Cited

U.S. PATENT DOCUMENTS

| | | | |
|---|---|---|---|
| 2,898,339 | 8/1959 | Wheeler et al. | 260/293.4 |
| 3,576,810 | 4/1971 | Duncan et al. | 424/267 |
| 3,687,956 | 8/1972 | Zivkovic | 424/267 |
| 3,806,526 | 4/1974 | Carr et al. | 424/267 |
| 3,922,276 | 11/1975 | Duncan et al. | 424/267 |
| 4,251,655 | 2/1981 | Scott et al. | 542/415 |
| 4,285,958 | 8/1981 | Carr et al. | 546/239 |

FOREIGN PATENT DOCUMENTS

| | | |
|---|---|---|
| 748568 | 4/1970 | Belgium . |
| 1106861 | 3/1968 | United Kingdom . |
| 1108033 | 3/1968 | United Kingdom . |
| 2068956 | 8/1981 | United Kingdom . |

*Primary Examiner*—Norma S. Milestone

*Attorney, Agent, or Firm*—Wenderoth, Lind & Ponack

[57] ABSTRACT

New 2-[4-(diphenylmethylene)-1-piperidinyl]-acetic acids and their amides, processes for the preparation thereof and therapeutic compositions. These compounds have the formula

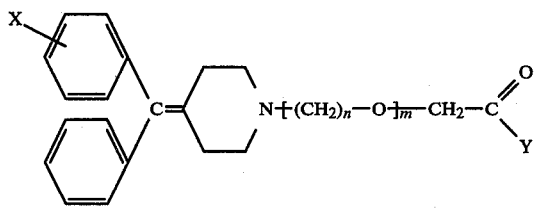

wherein Y=—OH or —NR$_1$R$_2$, R$_1$ and R$_2$=H, alkyl or phenyl; X=H, halogen or alkoxy; m=0, 1 or 2 and n=1 or 2.

The 2-[4-(diphenylmethylene)-1-piperidinyl]-acetic acids are prepared by hydrolyzing the corresponding amide or lower alkyl ester, whereas the amides are prepared either by reacting a 4-(diphenylmethylene)-piperidine with an omega-haloacetamide, or by reacting an alkali metal salt of an omega-[4-diphenylmethylene)-1-piperidinyl]-alkanol (m=1 or 2) with a 2-haloacetamide, or by reacting a nitrogen compound (HNR$_1$R$_2$) with a halide or alkyl ester of a 2-[4-(diphenylmethylene)-1-piperidinyl]-acetic acid.

These compounds have in particular an antiallergic, spasmolytic, antihistaminic and broncholytic activity.

4 Claims, No Drawings

2-[4-(DIPHENYLMETHYLENE)-1-PIPERIDINYL]-ACETIC ACIDS AND THEIR AMIDES

The present invention relates to new 2-[4-(diphenylmethylene)-1-piperidinyl]-acetic acids and their amides and non-toxic, pharmaceutically acceptable salts thereof, as well as to processes for the preparation thereof. It also relates to pharmaceutical compositions containing these new compounds.

The new compounds according to the present invention have the general formula:

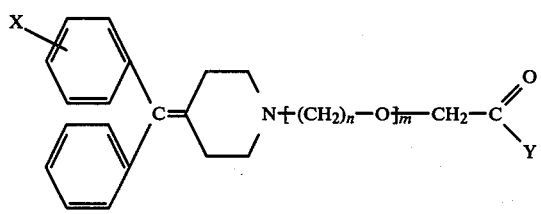

wherein
- Y is a hydroxyl group or an —NR$_1$R$_2$ group, in which R$_1$ and R$_2$ represent independently a hydrogen atom, a lower alkyl radical or a phenyl radical,
- X represents a hydrogen atom, a halogen atom or a lower alkoxy radical,
- m is 0, 1 or 2, preferably 1 or 2, and
- n is 1 or 2, preferably 2.

The term "lower alkyl" as used herein means both straight and branched chain aliphatic hydrocarbon radicals having from 1 to 4 carbon atoms, such as methyl, ethyl, propyl, isopropyl and butyl. Similarly, the term "lower alkoxy" means radicals such as methoxy, ethoxy, propoxy and the like having from 1 to 4 carbon atoms. The halogen atom is preferably a chlorine or fluorine atom.

The preferred compounds according to the present invention are:
- 2-[2-[2-[4-(diphenylmethylene)-1-piperidinyl]ethoxy]ethoxy]-acetic acid and the corresponding amide;
- 2-[2-[4-(diphenylmethylene)-1-piperidinyl]ethoxy]-acetic acid;
- 2-[2-[4-[(4-fluorophenyl)phenylmethylene]-1-piperidinyl]ethoxy]-acetic acid and the corresponding amide;
- 2-[2-[4-[(2-chlorophenyl)phenylmethylene]-1-piperidinyl]ethoxy]-acetic acid and the corresponding amide;
- 2-[2-[4-[(4-methoxyphenyl)phenylmethylene]-1-piperidinyl]ethoxy]-acetamide.

The compounds of formula I possess interesting pharmacological properties; in particular, they are useful as antiallergic, antihistaminic, bronchodilatory and antispasmodic agents.

Furthermore, secondary effects of stimulating or depressing the central nervous system, which are frequently observed with conventional antihistamines, are minimal. In addition, they are of interest as anaesthetics and antiinflammatory agents and they display an activity in cases of cerebral and cardiovascular insufficiency.

A. Processes for the preparation of the new compounds (I)

I. The acids of formula I, in which Y is a hydroxyl group, are prepared by the hydrolysis, in a basic medium, of a functional derivative of a 2-[4-(diphenylmethylene)-1-piperidinyl]-acetic acid, i.e. an amide or a lower alkyl ester of the formula:

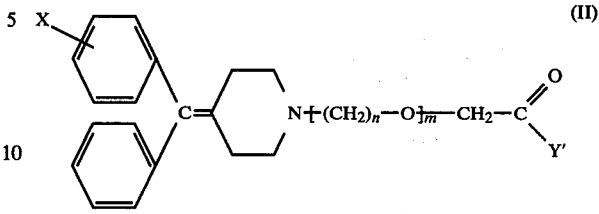

wherein X, m and n have the same meanings as above and Y' is an —NR$_1$R$_2$ group, R$_1$ and R$_2$ having the same meanings as above, or is an —OR' group, in which R' is a lower alkyl radical, for example a methyl or ethyl radical.

This hydrolysis is carried out with an inorganic base, for example sodium or potassium hydroxide, in an aqueous or aqueous alcoholic medium, the alcohol being, for example, methanol, ethanol or the like, at a temperature of from 20° C. up to the reflux temperature of the reaction mixture.

The esters of formula II, in which Y' is —OR', which are used as starting materials for the preparation of the acids according to the present invention by the above-described process, may be prepared by various methods, for example:

E.1 Reacting a 4-(diphenylmethylene)-piperidine of formula III with a lower alkyl omega-haloacetate of formula IV according to the following equation:

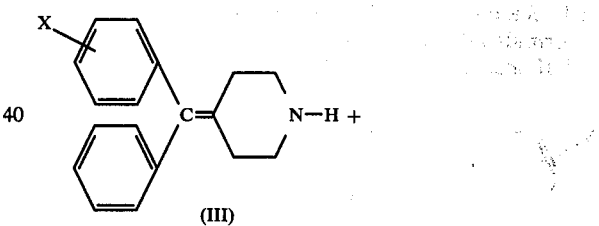

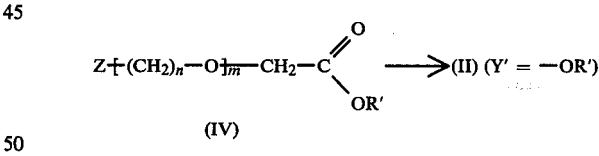

in which X, m and n have the same meanings as above, R' is a lower alkyl radical and Z is a halogen atom.

Thus, for example, R' may be a methyl or ethyl radical and Z may be a chlorine or bromine atom.

This reaction is generally carried out by heating to a temperature of from 80° to 150° C. for several hours, in an inert solvent selected from aliphatic alcohols, benzene, toluene and xylene, in the presence of an acid acceptor, such as a tertiary organic base, for example triethylamine, or an inorganic base, for example sodium carbonate.

E.2 When, in formula II, m is 1 or 2, reacting an alkali metal salt of an omega-[4-(diphenylmethylene)-1-piperidinyl]-alkanol of formula V with a lower alkyl haloacetate of formula VI according to the following equation:

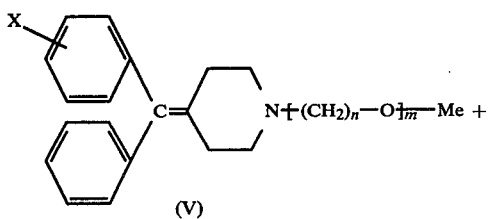

(V)

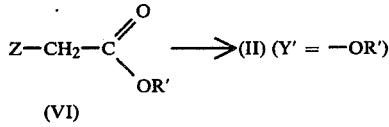

(VI)

in which R', X and n have the same meanings as above, m is 1 or 2, Z is a halogen atom and Me is an alkali metal.

The reaction between the metal salt of formula V and the haloacetate of formula VI is carried out in an inert solvent at a temperature of from 0° C. up to the reflux temperature of the reaction mixture.

The alkali metal salt used in this reaction can be prepared in situ by reacting an appropriate omega-[4-(diphenylmethylene)-1-piperidinyl]-alkanol with an alkali metal hydride, usually sodium hydride, in an inert solvent, for example toluene, xylene or dimethylformamide.

The preparation of the alkanols of formula V in which Me is a hydrogen atom is described in Belgian Patent Specification No. 748,568.

II. The amides of formula I, in which Y is an $-NR_1R_2$ group, may be prepared by various methods, namely:

II.1. Reacting a 4-(diphenylmethylene)-piperidine of formula III with an omega-haloacetamide of formula VII according to the following equation:

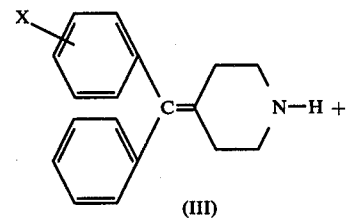

(III)

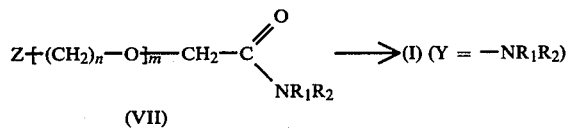

(VII)

in which $R_1$, $R_2$, X, m and n have the same meanings as above and Z is a halogen atom.

This reaction is generally carried out by heating the reaction mixture at a temperature of from 80° to 150° C. for several hours, in an inert solvent selected from aliphatic alcohols, benzene, toluene and xylene, in the presence of an acid acceptor, such as a tertiary organic base, for example triethylamine, or an inorganic base, for example sodium carbonate.

II.2. In the case of compounds of general formula I in which m is 1 or 2, reacting an alkali metal salt of an omega-[4-(diphenylmethylene)-1-piperidinyl]-alkanol of formula V with a 2-haloacetamide of formula VIII according to the following equation:

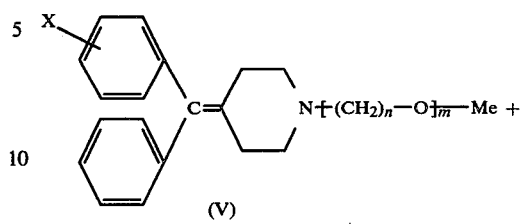

(V)

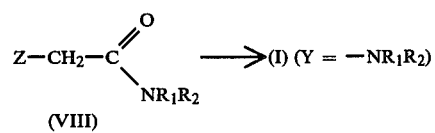

(VIII)

in which $R_1$, $R_2$, X and n have the same meanings as above, m is 1 or 2, Z is a halogen atom and Me is an alkali metal.

The reaction between the metal salt of formula V and the haloacetamide of formula VIII is carried out in an inert solvent, at a temperature of from 0° C. up to the reflux temperature of the reaction mixture.

II.3. Reacting a nitrogen compound of formula X with a functional derivative of a 2-[4-(diphenylmethylene)-1-piperidinyl]-acetic acid, i.e. a halide or a lower alkyl ester of formula IX, according to the following equation:

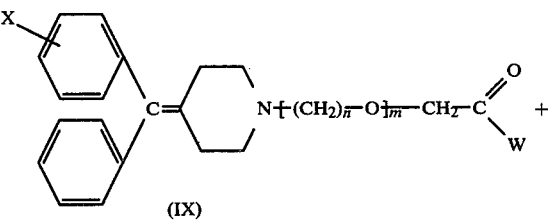

(IX)

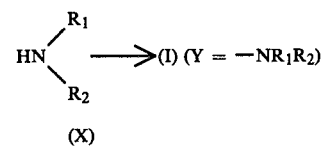

(X)

in which $R_1$, $R_2$, X, m and n have the same meanings as above and W is a halogen atom or an —OR' radical, in which R' is a lower alkyl radical.

The halogen atom may be, for example, a chlorine or bromine atom and the alkyl radical may be a methyl or ethyl radical.

When W is a halogen atom, an acid of formula I is first prepared by method I described above and then converted into a corresponding halide in a known manner. Thereafter, the halide thus obtained is reacted with an appropriate amine, in an inert solvent, in the presence of an acid acceptor, for example an organic or inorganic base.

When W is an —OR' radical, an ester of formula II is first prepared by one of the methods E.1 or E.2 described above. Thereafter, this ester is reacted with an apropriate amine, in an inert solvent, which may be an excess of the amine used, at a temperature of from ambient temperature up to the reflux temperature of the reaction mixture. This reaction may possibly be carried out in the presence of a catalyst, such as sodium methoxide. The operating conditions may be varied according to the nature and reactivity of the amine used.

The term "non-toxic, pharmaceutically acceptable salts" as used herein means not only the addition salts of the acids and amides of formula I with pharmaceutically acceptable acids, such as acetic, citric, succinic, ascorbic, hydrochloric, hydrobromic, sulfuric and phosphoric acid, but also the pharmaceutically acceptable salts of the acids of formula I, such as the metal salts, for example the sodium and potassium salts, the ammonium salts, the amine salts and the aminoacid salts.

These pharmaceutically acceptable salts may be prepared from compounds of formula I by known methods. The following Examples are given for the purpose of illustrating the present invention:

Example 1. Preparation of esters of formula II 1.1. Ethyl 2-[2-[2-[4-(diphenylmethylene)-1-piperidinyl]ethoxy]ethoxy]-acetate (method E.2)

A solution of 207.6 g (0.616 mole) of 2-[2-[4-(diphenylmethylene)-1-piperidinyl]ethoxy]-ethanol in 1.2 liters of anhydrous toluene is cooled to about 10° C. 17.5 g (0.729 mole) of sodium hydride (obtained from 35 g of a 50% suspension of sodium hydride in paraffin and which has been washed three times with anhydrous toluene) are added portionwise thereto.

The reaction mixture is slowly heated to about 40° C. and maintained at this temperature for 2 hours. It is then cooled to 0° C. under an atmosphere of nitrogen and, while maintaining this temperature, 122 g (0.73 mole) of ethyl bromoacetate are introduced. The initial reaction is violent. When the addition is complete, the reaction mixture is kept at 40° C. for 4 hours and then again cooled to ambient temperature. The reaction mixture is filtered and the precipitate is washed with a little toluene. The filtrate, after evaporation, gives 345.6 g of residue which is ethyl 2-[2-[2-[4-(diphenylmethylene)-1-piperidinyl]ethoxy]ethoxy]-acetate. This is then used as such in Example 3.1, without further purification.

1.2 The product of Example 1.1 may also be obtained under the following conditions (method E.1)

A mixture of 24.93 g of 4-(diphenylmethylene)-piperidine, 32 g of ethyl [2-(2-chloroethoxy)ethoxy]-acetate and 18 g of anhydrous sodium carbonate in 80 ml of xylene is heated for 20 hours at a temperature of from 90° to 110° C. The obtained precipitate is filtered off. The filtrate is extracted with dilute aqueous hydrochloric acid and the aqueous phase is rendered alkaline with a concentrated aqueous solution of sodium hydroxide and extracted with benzene. The benzene phase is evaporated in vacuo and the ester residue obtained is used as such in Example 3.2, without further purification.

The ethyl [2-(2-chloroethoxy)ethoxy]-acetate used in this synthesis is prepared in the following manner: a cold solution of 100 g of [2-(2-chloroethoxy)ethoxy]-acetonitrile in 500 ml of ethanol is saturated with gaseous hydrogen chloride. The reaction mixture is heated under reflux for 5 hours, followed by distillation. The yield is 81.2% of theory and the product has a boiling point of 146°-148° C./20 mbar.

1.3. Ethyl 2-[2-[4-(diphenylmethylene)-1-piperidinyl]ethoxy]-acetate

This ester is prepared by the method described in Example 1.2, starting from ethyl (2-chloroethoxy)-acetate and 4-(diphenylmethylene)-piperidine. It is not isolated but used as such, without further purification, for the preparation of the corresponding acid (see Example 3.3).

Example 2. Preparation of amides of formula I 2.1. 2-[2-[2-[4-(Diphenylmethylene)-1-piperidinyl]ethoxy]ethoxy]-acetamide (method II.1)

A mixture of 29.9 g of 4-(diphenylmethylene)-piperidine, 36.3 g of 2-[2-(2-chloroethoxy)ethoxy]-acetamide and 18 g of sodium carbonate in 80 ml of xylene is heated for 20 hours at a temperature of from 90° to 110° C. Thereafter, 80 ml of benzene are added thereto. The precipitate obtained is filtered off and the organic phase is extracted with a dilute solution of hydrochloric acid (20 ml of concentrated hydrochloride acid and 80 ml of water). After the addition of 30 ml of a concentrated solution of sodium hydroxide and extraction with benzene, the benzene solution obtained is washed, dried over anhydrous potassium carbonate and the benzene evaporated in vacuo. The 2-[2-[2-[4-(diphenylmethylene)-1-piperidinyl]ethoxy]ethoxy]-acetamide obtained is used as such for the preparation of the corresponding acid (see Example 3.4).

The 2-[2-(2-chloroethoxy)ethoxy]- acetamide used in this synthesis is prepared by the process described in British Patent Specification No. 1,357,547. The yield is 77% of theory; M.P. 51°-53° C.

2.2. 2-[2-[2-[4-(Diphenylmethylene)-1-piperidinyl]ethoxy]ethoxy]-acetamide hydrochloride (method II.3)

40 g of the ester obtained in Example 1.1 are dissolved in 400 ml of methanol. Therafter, ammonia is passed in overnight at ambient temperature. The solution is evaporated to dryness and the residue is redissolved in ethyl acetate. The solution is filtered over "Norite" and evaporated to dryness. The residue is dissolved in diethyl ether to which is added the stoichiometric amount of an ethereal solution of hydrochloric acid in order to convert the base into the hydrochloride. This is successively recrystallized from acetone and acetonitrile. Finally, there are obtained 11.5 g of 2-[2-[2[4-(diphenylmethylene)-1-piperidinyl]ethoxy]ethoxy]-acetamide hydrochloride; M.P. 145°-146° C. The yield is 28% of theory.

Analysis for $C_{24}H_{30}N_2O_3 \cdot HCl$ in %:

| | | | |
|---|---|---|---|
| calc.: C 66.9 | H 7.20 | N 6.50 | Cl⁻ 8.35 |
| found: 66.5 | 7.21 | 6.17 | 8.08 |

2.3. The following compounds are prepared by the method of Example 2.1

2-[4-(diphenylmethylene)-1-piperidinyl]-acetamide. yield 40% of theory; M.P. 220° C.

Analysis for $C_{20}H_{22}N_2O$ in %:

| | |
|---|---|
| calc.: C 78.40 | H 7.24  N 9.14 |

-continued

| Analysis for C20H22N2O in %: | | | |
| --- | --- | --- | --- |
| found: | 77.64 | 7.36 | 8.90 |

2-[4-[(4-chlorophenyl)phenylmethylene]1-piperidinyl]-acetamide hydrochloride yield 77% of theory; M.P. 221°–223° C.

| Analysis for C20H21ClN2O.HCl in %: | | | | |
| --- | --- | --- | --- | --- |
| calc.: | C 63.66 | H 5.87 | N 7.42 | Total Cl 18.79 |
| found: | 63.38 | 6.13 | 7.63 | 18.76 |

2-[2-[4-[(4-chlorophenyl)phenylmethylene]-1-piperidinyl]ethoxy]-acetamide hydrochloride yield 65% of theory; M.P. 166°–169° C.

| Analysis for C22H25ClN2O2.HCl in %: | | | | | |
| --- | --- | --- | --- | --- | --- |
| calc.: | C 62.74 | H 6.22 | N 6.65 | Cl⁻ 8.42 | Total Cl 16.83 |
| found: | 61.22 | 6.40 | 6.47 | 8.71 | 16.51 |

2-[2-[2-[4-[(4-chlorophenyl)phenylmethylene]-1-piperidinyl]ethoxy]ethoxy]-acetamide yield 93% of theory.

| Analysis for C24H29ClN2O3 in %: | | |
| --- | --- | --- |
| calc.: | N 6.53 | Cl 8.63 |
| found: | 5.59 | 8.74 |

Mass spectrum: molecular ion M+· at 428 m/e

2-[2-[4-[(2-chlorophenyl)phenylmethylene]-1-piperidinyl]ethoxy]-acetamide hydrochloride yield 86% of theory; M.P. 240°–241° C.

| Analysis for C22H25ClN2O2.HCl in %: | | | | | |
| --- | --- | --- | --- | --- | --- |
| calc.: | C 62.70 | H 6.21 | N 6.64 | Cl⁻ 8.41 | total Cl 16.82 |
| found: | 62.56 | 6.29 | 6.52 | 8.17 | 16.79 |

2-[2-[4-[(4-fluorophenyl)phenylmethylene]-1-piperidinyl]ethoxy]-acetamide.

yield 65% of theory; M.P. 118°–119° C.

| Analysis for C22H25FN2O2 in %: | | | |
| --- | --- | --- | --- |
| calc.: | C 71.71 | H 6.84 | N 7.60 |
| found: | 71.66 | 6.93 | 7.53 |

2-[2-[4-[(4-methoxyphenyl)phenylmethylene]-1-piperidinyl]ethoxy]-acetamide hydrochloride yield 47% of theory; M.P. 196°–198° C.

| Analysis for C23H28N2O3.HCl in %: | | | | |
| --- | --- | --- | --- | --- |
| calc.: | C 66.25 | H 7.01 | N 6.71 | Cl⁻ 8.50 |
| found: | 65.71 | 7.29 | 6.70 | 8.40 |

2.4.
2-[2-[2-[4-(Diphenylmethylene)-1-piperidinyl]ethoxy]ethoxy]-N-phenylacetamide hydrochloride (method II.3)

A solution of 0.85 ml of thionyl chloride in 10 ml of benzene is added to a suspension of 4.4 g of the acid hydrochloride obtained in Example 3.1 in 100 ml of anhydrous benzene. The reaction mixture is heated to 80° C. for 5 hours. Thereafter, it is evaporated to dryness to give 5.4 g of residue. This is taken up in 100 ml of chloroform and then there are successively added a solution of 1.01 g of triethylamine in 10 ml of chloroform and a solution of 0.93 g of aniline in 10 ml of chloroform, followed by the dropwise addition of a solution of 1.01 g of triethylamine in 25 ml of chloroform. The reaction mixture is stirred for 20 hours at ambient temperature, whereafter it is washed twice with water.

The organic phase is dried over anhydrous sodium sulfate, decolorized by filtering through "Norite" and then evaporated to dryness. The residue is converted into the hydrochloride by crystallization from a mixture of acetone and diethyl ether to which is added the stoichiometric amount of an ethanolic solution of hydrochloric acid. There is thus obtained 1.95 g of 2-[2-[2-[4-(diphenylmethylene)-1-piperidinyl]ethoxy]ethoxy9 -N-phenylacetamide hydrochloride. Yield 38% of theory; M.P. 133°–134° C.

| Analysis for C30H34N2O3.HCl in %: | | | |
| --- | --- | --- | --- |
| calc.: | C 71.07 | H 6.91 | N 5.53 |
| found: | 70.90 | 7.03 | 5.29 |

Example 3. Preparation of acids of formula I (Method I).

3.1.
2-[2-[2-[4-(Diphenylmethylene)-1-piperidinyl]ethoxy]ethoxy]-acetic acid hydrochloride 345.6 g of the ester obtained in Example 1.1 are dissolved in 0.9 liters of ethanol. This solution is added at 20° C. to a solution containing 288 g of potassium hydroxide in 1.5 liters of water. The alcohol is distilled off up to a temperature of 98° C. (column temperature). The reaction mixture is then evaporated to dryness and the residue is stirred into anhydrous toluene. Two phases are obtained and a little solid. The toluene phase is isolated and evaporated. There are obtained 291.5 g of residue. This is dissolved in 1.5 liters of isopropyl alcohol to which is added, at 20° C., 137 ml of a 4.91 N alcoholic solution of hydrochloric acid. The solution is evaporated to dryness and the residue is recrystallized from acetonitrile and then from isopropyl alcohol. There are thus obtained 104 g of 2-[2-[2-[4-(diphenylmethylene)-1-piperidinyl]ethoxy]-ethoxy]-acetic acid hydrochloride.

Yield 39% of theory; M.P. 139°–140° C.

| Analysis for C24H29NO4.HCl in %: | | | | |
| --- | --- | --- | --- | --- |
| calc.: | C 66.7 | N 6.95 | N 3.24 | Cl⁻ 8.40 |
| found: | 66.62 | 6.95 | 3.27 | 8.21 |

3.2. The acid obtained in Example 3.1 may also be prepared from the corresponding ester prepared in Example 1.2.

The ester residue obtained in Example 1.2, after evaporation in vacuo, is dissolved in 100 ml of ethanol and 23 ml of 3.95 N sodium hydroxide solution. After boiling under reflux for 1.5 hours, the reaction mixture is neutralized with 20.7 ml of 4.38 N hydrochloric acid and the ethanol is evaporated off in vacuo. The residue is extracted with dichloromethane and the organic phase, after drying over anhydrous sodium sulfate, is evaporated in dryness. The residue is stirred for 1 hour in 100 ml of ethyl acetate and then left to crystallize. There are obtained 13.4 g of 2-[2-[2-[4-(diphenylmethylene)-1-piperidinyl]ethoxy]ethoxy]-acetic acid. Yield 67.5% of theory; M.P. 120°–123° C.

3.3 The following compound is prepared by the method described in Example 3.2:

2-[2-[4-(diphenylmethylene)-1-piperidinyl]ethoxy]acetic acid hydrochloride

This compound is prepared from the ester obtained in Example 1.3. Yield 71% of theory; M.P. 193°–194° C.

Analysis for $C_{22}H_{25}NO_3 \cdot HCl$ in %:

| | | | | |
|---|---|---|---|---|
| calc.: | C 68.12 | H 6.75 | N 3.61 | $Cl^-$ 9.14 |
| found: | 67.37 | 6.78 | 3.56 | 8.93 |

3.4.
2-[2-[2-[4-(Diphenylmethylene)-1-piperidinyl]ethoxy]ethoxy]-acetic acid

The amide residue obtained in Example 2.1 is dissolved in 120 ml of ethanol. 60 ml of 3.95 N aqueous sodium hydroxide solution are added thereto and the reaction mixture is boiled for 1.5 hours. After cooling, it is neutralized by adding 54 ml of 4.38 N hydrochloric acid, whereafter the ethanol is evaporated off in vacuo. The resultant solution is extracted with dichloromethane, dried over anhydrous sodium sulfate and evaporated to dryness. The residue is stirred with 150 ml of ethyl acetate and left to crystallize. There are obtained 38 g of 2-[2-[2-[4-(diphenylmethylene)-1-piperidinyl]ethoxy]ethoxy]-acetic acid. The product obtained is identical to that prepared in Example 3.2. Yield 80% of theory; M.P. 121°–123° C.

Analysis for $C_{24}H_{29}NO_4$ in %:

| | | | |
|---|---|---|---|
| calc.: | C 72.88 | H 7.39 | N 3.54 |
| found: | 71.42 | 7.45 | 3.57 |

3.5. The following compounds are prepared by the method of Example 3.4 by the hydrolysis of the corresponding amide prepared in Example 2.3

2-[4-[(4-Chlorophenyl)-phenylmethylene]-1-piperidinyl]-acetic acid.

Yield 71% of theory; M.P. 190°–192° C.

Analysis for $C_{20}H_{20}ClNO_2$ in %:

| | | | | |
|---|---|---|---|---|
| calc.: | C 70.27 | H 5.90 | N 4.09 | Cl 10.37 |
| found: | 69.42 | 5.98 | 4.08 | 10.99 |

2-[2-[4-[(4-chlorophenyl)phenylmethylene]-1-piperidinyl]ethoxy]-acetic acid hydrochloride Yield 70% of theory; M.P. 166°–168° C.

Analysis for $C_{22}H_{24}ClNO_3 \cdot HCl$ in %:

| | | | | | |
|---|---|---|---|---|---|
| calc.: | C 62.56 | H 5.69 | N 3.31 | $Cl^-$ 8.39 | total Cl 16.78 |
| found: | 62.51 | 6.09 | 3.43 | 8.39 | 16.54 |

2-[2-[2-[4-[(4-chlorophenyl)phenylmethylene]-1-piperidinyl]ethoxy]ethoxy]acetic acid Yield 80% of theory; M.P. 112°–115°C.

Analysis for $C_{24}H_{28}ClNO_4$ in %:

| | | | | |
|---|---|---|---|---|
| calc.: | C 67.04 | H 6.56 | N 3.25 | Cl 8.55 |
| found: | 66.13 | 6.55 | 2.82 | 8.74 |

Mass spectrum: molecular ion $M^+$ at 429 m/e
The corresponding hydrochloride melts at 105°–108° C. (decomposition).

Analysis for $C_{24}H_{28}ClNO_4 \cdot HCl$ in %:

| | | |
|---|---|---|
| calc.: | $Cl^-$ 7.60 | total Cl 15.20 |
| found: | 6.99 | 15.20 |

2-[2-[4-[(2-chlorophenyl)phenylmethylene]-1-piperidinyl]ethoxy]-acetic acid hydrochloride.

Yield 94% of theory; M.P. 198°–200° C.

Analysis for $C_{22}H_{24}ClNO_3 \cdot HCl$ in %:

| | | | | | |
|---|---|---|---|---|---|
| calc.: | C 62.56 | H 5.96 | N 3.31 | $Cl^-$ 8.39 | total Cl 16.78 |
| found: | 62.51 | 5.80 | 3.30 | 8.35 | 17.36 |

2-[2-[4-[(4-fluorophenyl)phenylmethylene]-1-piperidinyl]ethoxy]-acetic acid

Yield 96% of theory; M.P. 72°–74° C.

Analysis for $C_{22}H_{24}FNO_3$ in %:

| | | | |
|---|---|---|---|
| calc.: | C 71.52 | H 6.52 | N 3.74 |
| found: | 71.05 | 6.05 | 3.90 |

Mass spectrum: molecular ion $M^+$ at 369 m/e

2-[2-[4-[(4-methoxyphenyl)phenylmethylene]-1-piperidinyl]ethoxy]-acetic acid hydrochloride Yield 65% of theory; M.P. 184°–187° C. (decomposition)

Analysis for $C_{28}H_{27}NO_4 \cdot HCl$ in %:

| | | | | |
|---|---|---|---|---|
| calc.: | C 66.17 | H 6.76 | N 3.35 | $Cl^-$ 8.49 |
| found: | 66.27 | 6.79 | 3.51 | 8.44 |

B. Pharmacology

The following compounds according to the present invention were subjected to pharmacological testing and gave the results described hereinafter:

2-[2-[2-[4-(diphenylmethylene)-1-piperidinyl]ethoxy]ethoxy]-acetic acid hydrochloride (compound A, prepared in Example 3.1);

2-[2-[4-(diphenylmethylene)-1-piperidinyl]ethoxy]-acetic acid hydrochloride (compound B, prepared in Example 3.3);

2-[2-[2-[4-(diphenylmethylene)-1-piperidinyl]ethoxy]ethoxy]-acetamide hydrochloride (compound C, prepared in Example 2.2);

2-[2-[4-[(4-chlorophenyl)phenylmethylene]-1-piperidinyl]ethoxy]-acetamide hydrochloride (compound D, prepared in Example 2.3);

2-[2-[2-[4-[(4-chlorophenyl)phenylmethylene]-1-piperidinyl]ethoxy]ethoxy]-acetamide (compound E, prepared in Example 2.3);

2-[2-[4-[(2-chlorophenyl)phenylmethylene-1-piperidinyl]ethoxy]-acetamide hydrochloride (compound F, prepared in Example 2.3);

2-[2-[4-[(4-fluorophenyl)phenylmethylene]-1-piperidinyl]ethoxy]-acetamide (compound G, prepared in Example 2.3);

2-[2-[4-[(4-methoxyphenyl)phenylmethylene]-1-piperidinyl]ethoxy]-acetamide hydrochloride (compound H, prepared in Example 2.3);

2-[2-[4-[(4-chlorophenyl)phenylmethylene]-1-piperidinyl]ethoxy]-acetic acid hydrochloride (compound I, prepared in Example 3.5);

2-[2-[2-[4-[(4-chlorophenyl)phenylmethylene]-1-piperidinyl]ethoxy]ethoxy]-acetic acid hydrochloride (compound J, prepared in Example 3.5);

2-[2-[4-[(2-chlorophenyl)phenylmethylene]-1-piperidinyl]ethoxy]-acetic acid hydrochloride (compound K, prepared in Example 3.5);

2-[2-[4-[(4-fluorophenyl)phenylmethylene]-1-piperidinyl]ethoxy]-acetic acid (compound L, prepared in Example 3.5);

2-[2-[4-[(4-methoxyphenyl)phenylmethylene]-1-piperidinyl]ethoxy]-acetic acid hydrochloride (compound M, prepared in Example 3.5);

2-[2-[2-[4-(diphenylmethylene)-1-piperidinyl]ethoxy]ethoxy]-N-phenylacetamide hydrochloride (compound N, prepared in Example 2.4).

1. Antiallergic activity

This activity is determined in rats by means of the passive cutaneous anaphylaxis test (PCA) (see J. Goose and A. M. J. N. Blair, Immunology,16, (1969),749–760; and U. Martin and D. Roemer, Arzneimittel-Forschung,28,(5), (1978),770–782).

Female rats are used, the sides of which have been partly shaved. Into the zone thus shaved there is injected intradermally, for passive sensitization of the animals, 0.05 ml of IGE antiovalbumin serum at a dilution such that, at the time of the PCA test, a distinct spot with a surface area of about 100 mm² appears at the point of injection.

72 Hours after the injection, 0.25 ml of a solution of allergen containing a coloring agent (5 mg of ovalbumin and 6 mg Evans Blue in 0.25 ml of a 0.9% aqueous solution of sodium chloride) is administered intravenously. At the point of intradermal injection, there appears a distinct blue spot, the surface of which is measured.

In order to test the activity of the compound according to the present invention, the procedure is carried out in the same manner; however:

the test compound is administered orally 72 hours after injection of the serum;

15 minutes after this administration, 0.25 ml of the solution of the allergen is injected intravenously;

30 minutes after the administration of the allergen, the surface of the blue spot is measured.

The following Table gives the immunological doses (ID 50 in μmol/kg) which bring about, on average of the total number of animals submitted to the test, a reduction of 50% of the surface area of the colored spot.

From this Table, it can be seen that the compounds of the present invention are active when administered per os, while sodium cromoglycate is inactive in this mode of administration, even though it is well known for its antiasthmatic activity when administered intravenously.

TABLE

| Test compound | ID 50 per os in μmol/kg |
|---|---|
| sodium cromoglycate | inactive |
| A | 133 |
| B | 39 |
| C | 76 |
| D | 67.4 |
| E | 34 |
| F | 66 |
| G | 5.5 |
| H | 31.4 |
| I | 100 |
| J | 100 |
| K | 100 |
| L | 34 |
| M | 208 |
| N | 15.2 |

2. Spasmolytic and antihistaminic activity.

These activities were measured in guinea pigs by the method of H. Konzett and R. Roessler (Naunyn-Schmiedebergs Arch.exp.Path.Pharmakol., 195,(1940),71–74) and compared with those of theophylline.

Anaesthetized and curarized guinea pigs are subjected to artificial ventilation. The endotracheal pressure is recorded. Repeated bronchial spasms are induced by successive and progressive intravenous injections of respectively acetylcholine, histamine and serotonin.

The test compounds are also administered intravenously.

The following Table shows the doses of the compound (in μg/kg) which inhibit 50%, on average of the total number of animals, of the induced bronchospasms:

TABLE

| Test compound | Serotonin | Histamine | Acetylcholine |
|---|---|---|---|
| A | 2560 | 2650 | 4130 |
| B | 206 | 37 | >82500 |
| C | 9 | 31 | 470 |
| E | 85 | 348 | >4285 |
| F | 55 | 551 | >1347 |
| G | 23 | 93 | >11776 |
| H | 180 | 26 | >41650 |
| I | 1177 | 413 | 13500 |
| J | 796 | 283 | >46600 |
| K | 430 | 104 | 39457 |
| L | 198 | 58 | >11810 |
| M | 893 | 181 | >41750 |
| N | 86 | 192 | 1347 |

It can be seen from this Table that, in comparison with theophylline, the compounds according to the present invention have a moderate spasmolytic activity towards the bronchospasms induced by acetylcholine but a remarkable activity with regard to the bronchospasms induced, respectively, by serotonin and histamine.

Furthermore, this test has shown that some of the compounds administered at a single dose possess an antihistaminic activity of long duration. Thus, for example, compound A, administered intravenously to guinea pigs at a dose of 1 mg/kg, has an antihistaminic activity of 100% after 90 minutes and retains this activity 4 hours after injection.

3. Broncholytic activity

This activity is evaluated in dogs by means of the "pilocarpine dog" test (see J. Mead and J. L. Whittenberger, J.appl.Physiol.5,(1953),779-796) and J. Lulling et al., Med.Pharmacol.Exp.,16,(1967),481-495).

Anaesthetized and curarized dogs are subjected to artificial ventilation. The endotracheal pressure is recorded. A constant respiratory spasm is induced by the continuous intravenous perfusion of pilocarpine. The test substances are also administered intravenously.

At the dose of 320 μg/kg, compound A reduces by 50%, on average of the total number of animals submitted to the test, the intensity of the induced spasm.

By way of comparison, theophylline injected at the tenfold dose of 3200 μg/kg, only reduces the intensity of the induced spasm by 35%.

It appears that compound A of the present invention has a broncholytic activity which is clearly superior to that of theophylline.

4. General behaviour of mice (Irwin's test)

The behaviour is studied by means of Irwin's test (see S. Irwin, "General philosophy and methodology of screening: a multidimensional approach"; Gordon Research Conference on Medicinal Chemistry, Aug. 3-7, 1959, at Colby Junior College, New London).

Progressive doses of the test compounds are administered intraperitoneally to groups of three male mice (body weight 18 to 22 g) and the general behaviour of the animals is observed according to known criteria. The reference compounds used are the following:
hydroxyzine=1-(p-chloro-alpha-phenylbenzyl)-4-(2-hydroxyethoxyethyl)piperazine,
oxazepam=7-chloro-1,3-dihydro-3-hydroxy-5-phenyl-2H-1,4-benzodiazepin-2-one.

The following Table gives the doses (in mg/kg) which induce the first manifestations of tranquilization in the animals:

TABLE

| Test compound | "Tranquilizing" dose (in mg/kg) |
|---|---|
| A | 130 |
| B | 105 |
| F | no sedative effect at all |
| I | 76 |
| J | 47 |
| K | 126 |
| L | 110 |
| M | 125 |
| Hydroxyzine | 27 |
| Oxazepam | 2.6 |

It can be seen from this Table that the compounds according to the present invention have little sedative effect in comparison with the reference compounds (the doses of the latter are clearly lower).

Furthermore, in this test, the toxicity of the compounds according to the present invention appears to be very low. This toxicity, determined by intraperitoneal administration in mice (dose which brings about the death of two animals out of three), is given in the following Table:

TABLE

| Test compound | Toxicity (in mg/kg) |
|---|---|
| A | 432 |
| B | 233 |
| C | 258 |
| D | 126 |
| E | 128 |
| F | 421 |
| G | 368 |
| H | 416 |
| I | 844 |
| J | 140 |
| K | 422 |
| L | 369 |
| M | 418 |

5. Toxicity

The compounds according to the present invention have a very low toxicity. The toxicity $LD_{50}$ (in mg/kg) is determined by oral administration to rats and mice. Thus, in the case of compound A, this toxicity is 1903 mg/kg in rats and 959 mg/kg in mice.

6. Posology and administration

The pharmaceutical compositions containing the compounds of the present invention may be administered orally, parenterally or rectally. They may also be administered by nasal instillation (aerosols) or in the form of unguents or creams. The pharmaceutical compositions which can be used for oral administration may be solid or liquid, for example, in the form of uncoated or coated tablets, pills, dragees, gelatine capsules, solutions, syrups and the like. The compositions which can be used for parenteral administration can be any of those pharmaceutical compositions known for this mode of administration, for example, aqueous or oily solutions, suspensions or emulsions. For administration by the rectal route, the compositions containing the compounds of the present invention are generally used in the form of suppositories.

The pharmaceutical forms such as injectable solutions, injectable suspensions, tablets, drops, suppositories and the like are prepared by conventional pharmaceutical methods. The compounds of the present invention are mixed with a solid or liquid carrier which is non-toxic and pharmaceutically acceptable, and possibly also mixed with a dispersing agent, a disintegrating agent, a stabilizing agent and the like. If appropriate, it is also possible to add preservatives, sweeteners, coloring agents and the like. The percentage of active compound in the pharmaceutical compositions may be varied within wide limits, according to the patient and the mode of administration and, in particular, the frequency of administration.

With regard to the posology, it may be varied within a wide range of dosage units, for example from 0.5 to 500 mg of active compound. Thus, the desired effects can be obtained by administering intravenously a single dose of 30 mg or, orally, a 100 mg gelatine capsule once or twice a day.

The following Examples illustrate the pharmaceutical compositions containing the compounds according to the present invention:

Example A

Formulation for an ampule for intravenous administration

| | |
|---|---|
| Compound A | 50 mg |
| sodium chloride | 90 mg |
| sodium acetate | 20 mg |
| sodium hydroxide | to adjust the pH to 5.5 |
| distilled water | 10 ml |

In the same way, use may be made of 10 ml ampules containing respectively 4, 20, 30 or 200 mg of active compound.

Example B

Gelatine capsule for oral administration

| | |
|---|---|
| Compound A | 100 mg |
| lactose | 344 mg |
| cellulose (Avicel) | 50 mg |
| silicon dioxide (Aerosil) | 1 mg |
| magnesium stearate | 5 mg |

In the same way, use may also be made of gelatine capsules containing 10 or 50 mg of active compound.

We claim:

1. 2-[2-[2-[4-(diphenylmethylene)-1-piperidinyl]ethoxy]ethoxy]-acetic acid or a non-toxic pharmaceutically acceptable salt thereof.

2. A compound as claimed in claim 1, namely 2-[2-[2-[4-(diphenylmethylene)-1-piperidinyl]ethoxy]ethoxy]-acetic acid hydrochloride.

3. A pharmaceutical composition comprising a therapeutically effective amount of a compound as claimed in claim 1 and a pharmaceutically acceptable solid or liquid diluent or carrier therefor.

4. A pharmaceutical composition comprising a therapeutically effective amount of a compound as claimed in claim 2 and a pharmaceutically acceptable solid or liquid diluent or carrier therefor.

* * * * *